United States Patent [19]

Ikegami

[11] Patent Number: 5,753,914

[45] Date of Patent: May 19, 1998

[54] METHOD AND APPARATUS FOR INVESTIGATING THE PHYSICAL PROPERTIES OF MATERIAL SURFACE LAYER

[75] Inventor: Hidetsugu Ikegami, Takarazuka, Japan

[73] Assignee: Japan Science and Technology Corporation, Japan

[21] Appl. No.: 844,107

[22] Filed: Apr. 28, 1997

[30] Foreign Application Priority Data

Jul. 16, 1996 [JP] Japan ................................. 8-185686

[51] Int. Cl.$^6$ ..................... H01J 37/252; G01N 23/225
[52] U.S. Cl. ........................ 250/309; 250/308; 250/307
[58] Field of Search ............................ 250/309, 307, 250/308

[56] References Cited

U.S. PATENT DOCUMENTS

| | | | |
|---|---|---|---|
| 5,063,293 | 11/1991 | Rich et al. | 250/308 |
| 5,159,195 | 10/1992 | Van House | 250/309 |
| 5,200,619 | 4/1993 | Asokakumar et al. | 250/307 |

FOREIGN PATENT DOCUMENTS 405010895A  1/1993  Japan.

*Primary Examiner*—Jack I. Berman
*Attorney, Agent, or Firm*—Lorusso & Loud

[57] ABSTRACT

An improved method is disclosed which investigates the surface layer of a material. A pulsed slow positron beam having a pulse duration in a nanosecond range is focused and irradiated on the reverse surface of a thin-film-like sample, and a probe is brought into contact with the front surface of the sample. Surface positrons are swarmed in a gap space at the contact point so as to form positronium molecules $Ps_n$ (n is an integer equal to or greater than 2). Coherent annihilation gamma-rays generated due to annihilation of the positronium molecules $Ps_n$ are detected so as to discriminate the positronium molecules $Ps_n$ from positrons and positroniums Ps, thereby measuring on an atomic scale the physical properties of the surface layer of the material with a response time shorter than 1 nanosecond. This method makes it possible to measure on an atomic scale the state of local electrons at a surface layer of a material and activities at the surface layer, such as catalytic activity, with a response time shorter than 1 nanosecond.

4 Claims, 1 Drawing Sheet

F I G. 1
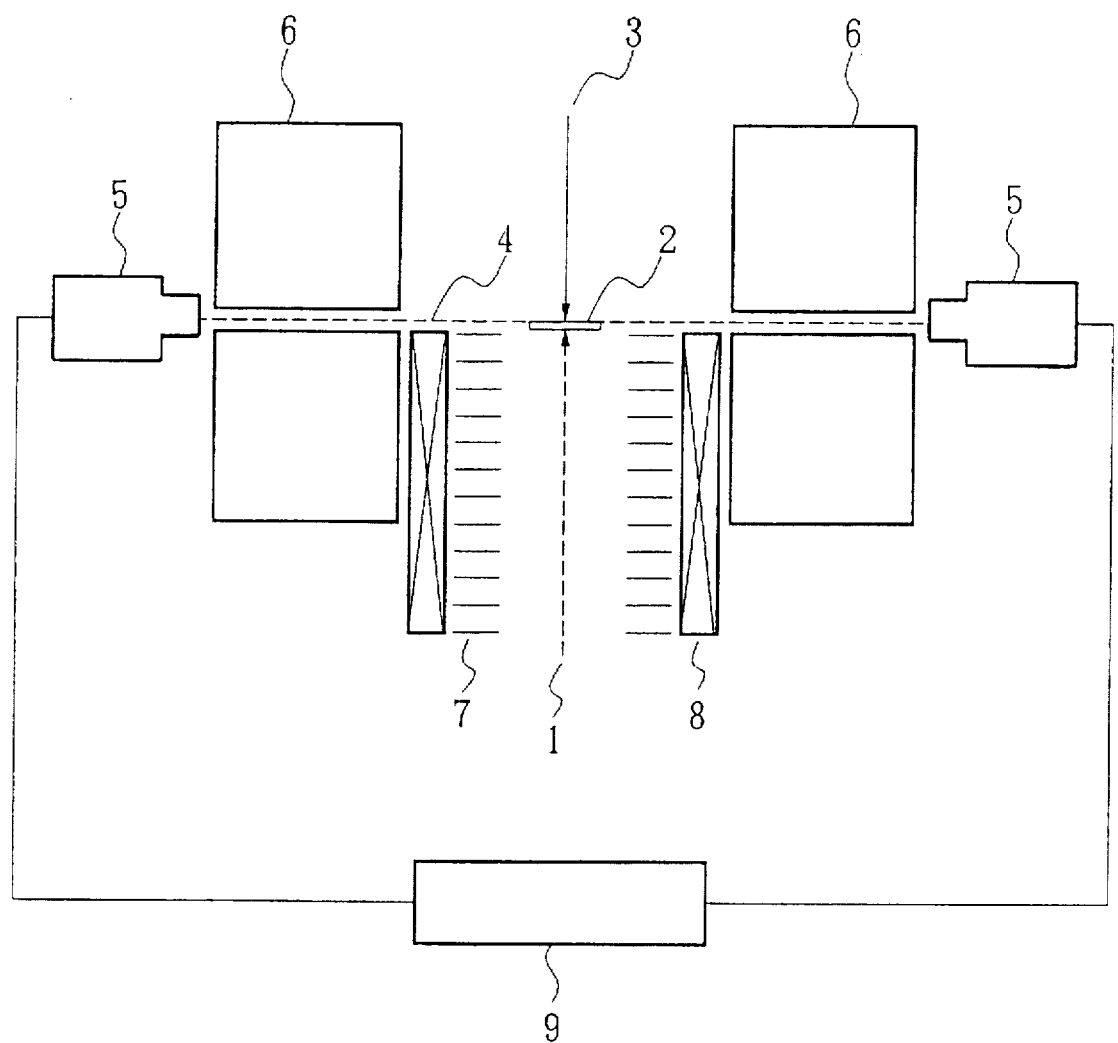

METHOD AND APPARATUS FOR INVESTIGATING THE PHYSICAL PROPERTIES OF MATERIAL SURFACE LAYER

BACKGROUND OF THE INVENTION

1. Field of the Invention

The present invention relates to a method and apparatus for investigating on an atomic scale not only the state of local electrons but also catalytic activity and other activities at the surface layer of a new material or the like, with a response time shorter than one nanosecond.

2. Description of the Related Art

Observation of positron annihilation gamma-rays, which is very effective in the investigation of bulk crystals or the like has provided important information on the state of local electrons inside or at the surface of a sample, which are averaged in terms of time and space. However, since there has been no method of determining on an atomic scale the location where a positron annihilation gamma-ray is generated, it has been impossible to investigate microscopically activities such as catalytic activity at the surface layer of a sample.

Therefore, there has been a problem that the activities such as catalytic activity at the surface layer or at an interface of a material cannot be investigated on an atomic scale with a response time shorter than 1 nanosecond.

SUMMARY OF THE INVENTION

An object of the present invention is to solve the above-described problems and to provide an improved method and apparatus for investigating on an atomic scale the physical properties of a surface layer of a material, thereby making it possible to observe on an atomic scale the state of local electrons and activities such as catalytic activity at the surface layer or at an interface of a sample, with a response time shorter than 1 nanosecond.

In order to achieve the above object, according to the present invention:

(1) positronium molecules $Ps_n$ are used as a probe which allows high sensitivity measurement of the physical properties of a material surface layer, in particular, activities such as catalytic activity with high sensitivity;

(2) in order to selectively detect a positronium molecule $Ps_n$, there is used a coherent annihilation gamma-ray that is generated due to coherent photon annihilation in which all positroniums Ps that constitute the positronium molecule $Ps_n$ simultaneously annihilate in the same phase; and (3) there is changed on an atomic scale the location where a positronium molecule $Ps_n$ is formed for the atomic scale investigation of the activity of the material surface layer.

BRIEF DESCRIPTION OF THE DRAWINGS

FIG. 1 shows a schematic layout diagram of a scanning positronium-molecular microscope according to an embodiment of the present invention in which pulses of a slow positron beam have an energy of a few keV to a few tens of keV and a duration in the nanosecond range.

DESCRIPTION OF THE PREFERRED EMBODIMENTS

Embodiments of the present invention will now be described below in detail.

(1) Positronium molecules $Ps_n$ serve as an ideal probe that makes it possible to observe, on an atomic scale, activities at a material surface layer. The positronium molecule $Ps_n$ is a molecule composed of n positroniums Ps, which are the lightest atoms, and consists of n positrons and n electrons. Among the positronium molecules $Ps_n$, a positronium molecule whose degree of clustering n is 2 is called dipositronium and is the lightest molecule in the universe.

(2) The possibility of the presence of the dipositronium $Ps_2$ was pointed out a half century ago (see "E. A. Hylleraas and A. Ore, Phys. Rev. 71, 493 (1947)"). Since then, many theoretical studies have been conducted regarding the shape and binding energy of the dipositronium $Ps_2$. However, since no method of detecting the dipositronium is known, the dipositronium has not yet been observed.

(3) The shape and binding energy of a stable dipositronium $PS_2$ can be determined through use of the condition for minimizing the internal energy of the dipositronium $Ps_2$ that is the sum of the zero-point energy; i.e., the kinetic energy and the potential energy. Here, the kinetic energy is obtained through quantization of each angular momentum for the respective three orthogonal axis passing through the center of mass of $Ps_2$ into $h/\pi$, where h is Plank's constant.

(4) The thus-obtained results are in good agreement with the numerical solutions obtained through computer calculations reported to date. The results can be summarized as follows.

(a) In a dipositronium $Ps_2$ isolated in vacuum, two p-Ps (para positroniums) or two o-Ps (ortho positroniums) are coupled with each other with a weak binding energy B given by the following relation:

$$B=2E(Ps)-E(Ps_2)=0.4\ eV, \tag{1}$$

wherein E(Ps) is the total energy of Ps, and $E(Ps_2)$ is the total energy of $Ps_2$. Therefore, $PS_2$ is stable only at the ground state.

(b) The dipositronium $PS_2$ has a shape similar to a regular tetrahedron or pyramid-like shape in which each side has a length of:

$$r_{ev} \geq r_{od} = 6\ a_o = 3.2\ \text{Å} = 0.32 nm,$$

wherein $r_{ev}$ and $r_{od}$ are means spacings between the nearest neighbors with the same sign of charge and those of opposite sign of charge, respectively, and $a_o$ is the Bohr radius.

(c) Due to the very small binding energy B, the electron density $n(Ps_2)$ within $Ps_2$, or the density of electrons at the position of the positron, becomes almost the same as the electron density n(Ps) within Ps. Therefore, the annihilation rates of p-Ps and o-Ps within $Ps_2$ are in proportion to $n(Ps_2)$ and are respectively the same as those of isolated p-Ps and o-Ps except the statistical factors. The particularly important result is that the spacing between two Ps within $PS_2$ is shorter than the deBroglie wavelength, so therefore they are coherent, i.e., in the same phase like the Bose-Einstein condensation. Since Ps is a basic ionic-bond atom, the above consideration on the configuration of $Ps_2$ can be applied to $Ps_n$, where n>2. Therefore, in the decay mode of $Ps_n$, in addition to the two-photon annihilation rate $\lambda(Ps_n \rightarrow 2\gamma,\ Ps_{n-1})$ which represents the probability at which each Ps within $Ps_n$ annihilates independently, there must be considered the coherent 2n-photon annihilation rate $\lambda(Ps_n \rightarrow 2n\gamma)$ which represents the probability at which positroniums Ps in a number of n simultaneously annihilate yielding n coherent photon pairs in the same directions.

(5) The probability $\lambda(Ps_n \to 2\gamma, Ps_{n-1})$ at which any one of the positroniums Ps within a positronium molecule $Ps_n$ is n times the annihilation rate of an individual Ps is represented by the following equation:

$$\lambda(Ps_n \to 2\gamma, Ps_{n-1}) = n\lambda(Ps \to 2\gamma) \quad (3)$$

When n positroniums Ps cause coherent photon annihilation in the same phase, the amplitude of annihilation instead of probability becomes n times that of a single positronium; therefore the probability is represented by the following equation:

$$\lambda(Ps_n \to 2n\gamma) = n^2 \lambda(Ps \to 2\gamma), \quad (4)$$

or $$\lambda(Ps_n \to 2n\gamma) = n \lambda(Ps_n \to 2\gamma, Ps_{n-1}). \quad (5)$$

This leads to the conclusion that more than half of the positronium molecules $Ps_n$ cause coherent annihilation.

In coherent annihilation, n pairs of photons are radiated at the same time and in the same directions. Therefore, when such coherent annihilation is observed through use of an ordinary gamma-ray detector, the coherent annihilation is detected as if it were a two-photon annihilation having an energy of n×511 keV; i.e., n times the energy of an annihilation gamma ray.

(6) From the above consideration, it is found that through measurement of the spectrum distribution of a annihilation gamma ray, the degree of clustering n of a positronium molecule $Ps_n$ is determined from the energy of the gamma ray, and the formation rate of $Ps_n$ can be determined based on the spectrum intensity distribution of the gamma ray.

Next, with reference to FIG. 1, a description will be given of an embodiment in which positronium molecules $Ps_n$ serving as a probe are utilized so as to investigate on an atomic scale the physical properties of the surface layer of a material, in particular, activities such as catalytic activity.

FIG. 1 shows a schematic layout diagram of a scanning positronium-molecular microscope according to an embodiment of the present invention in which pulses of a slow positron beam have an energy of a few keV to a few tens of keV and a duration time in the nanosecond range.

In FIG. 1, numeral 1 denotes a slow positron beam, numeral 2 denotes a thin film sample, numeral 3 denotes a probe, numeral 4 denotes a coherent annihilation photon pair, numeral 5 denotes an annihilation gamma ray (photon) detector, numeral 6 denotes a radiation shield, numeral 7 denotes a positron beam focusing electrode system, numeral 8 denotes a solenoid coil, and numeral 9 denotes a coincidence annihilation gamma-ray spectrum analyzer.

The thickness of the thin film sample 2 is set to approximately 0.1 μm so as to allow the slow positron beam 1 to pass through the sample 2. The slow positron beam 1 is irradiated onto the reverse surface of the sample 2 such that it converges on the reverse surface. At the convergence point, the beam 1 has a diameter corresponding to the thickness of the sample 2.

A considerable portion of the irradiated positrons swarm at the front and reverse surface of the thin film sample 2 in the form of surface positrons. Surface positrons refer to thermal positrons which are bound to the surface by their image potential.

When the potential difference between the probe 3 and the thin film sample 2 is properly adjusted, the surface positrons swarm in a very small gap space between the tip of the probe 3 and the thin film sample 2, so that the positrons are coupled with electrons to form positroniums Ps and positronium molecules $Ps_n$.

The rate Z(Ps) of positronium Ps formation at the surface can be obtained on the basis of thermodynamics. That is, the positronium formation rate Z(Ps) is obtained in accordance with the following equation:

$$Z(Ps) = (hm_o n_o / 2\pi m_+^2)(1 - r_1) \exp(-E_a / kT) \quad (6)$$

wherein $m_o$ is the mass of an electron, $m_+$ is the effective mass of a surface positron, $E_a$ is the mean energy with which the positronium Ps is bound to the sample surface, k is Boltzmann's constant, T is the temperature of the surface layer of the sample, $r_1$ is an average value of the reflection coefficient of the positronium Ps at the sample surface, and $n_o$ is the critical density of the surface positrons. The critical density $n_o$ of the surface positrons is given by the following expression:

$$n_o = 8\pi^2 m_+ kT/h^2. \quad (7)$$

At the surface layer of the material, a dipositronium $Ps_2$ is formed through interaction between two surface positrons. The thermodynamically-obtained formation rate ($Ps_2$) is expressed as follows:

$$Z(Ps_2) = (hm_o n_+ / 2\pi m_+^2)(1 - r_2) \exp(B - 2E_a / kT) \quad (8)$$

wherein $r_2$ is an average value of the reflection coefficient of the dipositronium $Ps_2$ at the sample surface, and $n_+$ is the density of surface positrons. The value of B, which represents the binding energy of the positroniums Ps within the dipositronium $Ps_2$, may slightly deviate from the value of Equation (1) depending on the state of the surface layer.

From Equations (7) and (8), the formation ratio between Ps and $Ps_2$ synthesized at the surface layer of the material becomes as follows:

$$Z(Ps_2)/Z(Ps) = (n_+/n_o)(1 - r_2/1 - r_1) \exp[(B - E_a)/kT] \quad (9)$$

Since the value of $E_a$ varies depending on the surface treatment of the sample, the formation ratio varies sensitively with the condition of the surface layer of the sample; such as chemical activity through exponential dependence on (B−$E_a$). For example, in the case where surface positrons of $n_+ \approx 10^5$ cm$^{-2}$ swarm around the tip of the probe at the surface layer of $r_1 \approx r_2$ and $E_a \approx 0.1$ eV, at temperatures below the freezing point, the formation of dipositronium $Ps_2$ of B≈0.4 eV drastically increases with a decrease in temperature. At the temperature of liquid nitrogen, more dipositroniums $Ps_2$ than positroniums Ps are formed. Needless to say, the above-described discussion regarding the dipositroniums $Ps_2$ can be applied to positronium molecules having a larger degree of clustering of positroniums (n>2).

The formation of the positronium molecules $Ps_n$ is greatly affected by absorbed molecules on the surface of the sample, and by the state of the outermost layer such as fine defects, as well as by the local densities of the surface positrons and electrons at the surface. Accordingly, adjustment of very small potential difference between the probe 3 and the thin film sample 2 makes it possible to change the density of the surface positrons so as to change the formation rate of the positronium molecules $Ps_n$ and the spectrum of the degree of clustering n. The time dependence of the formation rate and the degree of clustering of the positronium molecules $Ps_n$ can be investigated by changing the intensity and pulse duration of the slow positron beam 1.

The molecular axes of the positronium molecule $Ps_n$ formed at the surface layer of the sample; i.e., the axes that connect the centers of the components Ps within the $Ps_n$ are parallel to the surface layer of the sample, because the image potential which traps the positronium molecule $Ps_n$ at the surface layer is planar. Since coherent annihilation photon pairs 4 are generally radiated along the molecular axes in opposite directions, the coherent annihilation photon pairs 4 of the positronium molecules $Ps_n$ formed at the surface layer of the sample are radiated in only directions parallel to the surface layer, so that the detection efficiency can be greatly gained through arrangement of the detector as shown in FIG. 1, as compared to an ordinary arrangement in which annihilation photon pairs are uniformly radiated into space.

Since positronium molecules $Ps_n$ are formed in a very small space and the positronium molecules $Ps_n$ formed are selectively detected at high efficiency, it is easy to trace the formation point while changing it on an atomic scale through super-microdrive, i.e., piezodrive of the probe. Therefore, it becomes possible to investigate variations with time and spatial distribution of the activities of the outermost layer of the sample. This becomes a powerful means for developing new materials.

The slow positron beam 1 is repeatedly irradiated to provide pulses each having a duration of 1 nanosecond or less. This makes it possible to measure tunneling current that flows through the probe during a period between the pulses. Accordingly, in addition to the function for observing positronium molecules $Ps_n$, the apparatus of the present invention can have a function of serving as a scanning probe microscope of a different type such as a scanning tunneling microscope, so that various kinds of information can be obtained simultaneously on an atomic scale.

The present invention is not limited to the embodiments described above. Numerous modifications and variations of the present invention are possible in light of the spirit of the invention. For example, the slow positron beam may be irradiated onto the front surface of the sample with which the probe is contacted.

The present invention provides the following advantages:

(A) A pulsed slow positron beam having a pulse duration in a nanosecond range is focused and irradiated on the reverse surface of a thin-film-like sample of a material, a probe is brought into contact with the front surface of the sample such that the probe faces the irradiated slow positron beam. The probe is driven in the same manner as in a scanning tunneling microscope. Surface positrons are swarmed in a gap space at the contact point so as to form positronium molecules $Ps_n$, and coherent annihilation gamma-rays generated due to annihilation of the positronium molecules are detected, thereby selectively observing the $Ps_n$. Subsequently, the intensity of the coherent annihilation gamma-rays is compared with the intensity of other positron annihilation gamma-rays, so that it becomes possible to measure on an atomic scale the physical properties of the outermost layer of a material, in particular, activities such as catalytic activity, with a response time shorter than 1 nanosecond.

(B) Since the scanning positronium-molecular microscope can have a function of serving as a scanning probe microscope of a different kind, variety kinds of information can be obtained on an atomic scale.

What is claimed is:

1. A method of investigating the surface layer of a material, wherein a pulsed slow positron beam having a pulse duration in a nanosecond range is focused and irradiated on the reverse surface of a thin-film-like sample of the material, a horizontally movable probe is brought into contact with the front surface of the sample such that the probe faces the focused slow positron beam, surface positrons are swarmed in a gap space at the contact point so as to form positronium molecules $Ps_n$ (n is an integer equal to or greater than 2), and coherent annihilation gamma-rays generated due to annihilation of the positronium molecules $Ps_n$ are detected so as to discriminate the positronium molecules $Ps_n$ from positrons and positroniums Ps, thereby measuring on an atomic scale the dynamical properties of the surface layer of the material with a response time shorter than 1 nanosecond.

2. A method of investigating the surface layer of a material according to claim 1, wherein the location of formation of positronium molecules $Ps_n$ is moved on an atomic scale by changing the position of the probe, and the spectrum of coherent annihilation gamma-rays generated due to annihilation of the positronium molecules $Ps_n$ is measured through scanning observation so as to determine the location and duration of formation of the positronium molecule $Ps_n$ as well as the degree of clustering n of the positronium molecule $Ps_n$, thereby measuring the activity of the surface layer of the material on an atomic scale.

3. A scanning positronium molecular microscope, comprising:

(a) means for focusing and irradiating, on the reverse surface of a thin-film-like sample of a material, a pulsed slow positron beam having a pulse duration in a nanosecond range;

(b) a probe which is in contact with the front surface of the sample such that the probe faces the focused slow positron beam, the probe being movable horizontally along the surface of the sample;

(c) annihilation gamma-ray detectors; and (d) coincidence annihilation gamma-ray spectrum analyzer connected to the annihilation gamma-ray detectors, wherein (e) surface positrons are swarmed in a gap space at the contact point so as to form positronium molecules $Ps_n$ (n is an integer equal to or greater than 2), and coherent annihilation gamma-rays generated due to annihilation of the positronium molecules $Ps_n$ are detected so as to discriminate the positronium molecules $Ps_n$ from positrons and positroniums Ps, thereby measuring on an atomic scale the dynamical properties of the surface layer of the material with a response time shorter than 1 nanosecond.

4. A scanning positronium-molecular microscope according to claim 3, further having a function of serving as a scanning probe microscope of a different type such as a scanning tunneling microscope so as to simultaneously perform investigation by scanning of positronium molecules and another investigation by the function of serving as the different type scanning probe microscope.

* * * * *